US00PP14447P39

(12) United States Plant Patent
Ackerman et al.

(10) Patent No.: US PP14,447 P3
(45) Date of Patent: Jan. 6, 2004

(54) STRAWBERRY PLANT NAMED 'PS-3523'

(50) Latin Name: *Fragaria ananassa*
Varietal Denomination: PS-3523

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 10/392,909

(22) Filed: Mar. 21, 2003

(65) Prior Publication Data

US 2003/0192094 P1 Oct. 9, 2003

Related U.S. Application Data

(60) Provisional application No. 60/368,123, filed on Mar. 29, 2002.

(51) Int. Cl.[7] ..... A01H 5/00

(52) U.S. Cl. ..... Plt./209

(58) Field of Search ..... Plt./209

*Primary Examiner*—Bruce R. Campell
*Assistant Examiner*—Michelle Kizilkaya
(74) *Attorney, Agent, or Firm*—Foley & Lardner

(57) ABSTRACT

This invention relates to a new and distinct everbearing variety of strawberry plant named 'PS-3523' primarily adapted to the growing conditions of the central coast of California. The new variety is primarily characterized by medium to large size plant, strong vigor, high number of crowns per plant, strong leaf gloss, deep serrations, medium to large stipules, few runners, longer than broad fruit, small seed, conical fruit shape, marked to moderate differences in shape between primary and secondary fruit, orange red fruit color, very good fruit gloss and skin firmness, slightly reflexed calyx, long pedicels and peduncles, long fruiting trusses and fruit and flowers characteristically above the foliage.

5 Drawing Sheets

Latin name of the genus and species of the plant claimed: *Fragaria ananassa.*

Variety denomination: Strawberry plant named 'PS-3523'.

BACKGROUND OF THE INVENTION

The present invention relates to a new and distinct everbearing strawberry variety designated as 'PS-3523'. This new variety is a result of a controlled cross made in 1995 between 'PS-592' (U.S. Plant Pat. No. 9,903) and 'PS-118' (U.S. Plant Pat. No. 8,205). The variety is botanically known as *Fragaria ananassa*. The new variety was discovered by the inventors, Stephen M. Ackerman, Steven D. Nelson, and Michael D. Nelson.

The seedling resulting from the aforementioned cross was asexually propagated by stolons in a nursery located in Siskiyou County, Calif., and was subsequently selected from a controlled breeding plot in Salinas, Calif. in 1997. After its selection, the new variety was further asexually propagated in both Siskiyou County, Calif. and San Joaquin County, Calif. by stolons. The new variety was then extensively tested over the next several years in the fruiting fields of Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-3523' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and moderate temperatures to maintain fruit quality during the spring and summer production months. The following list of traits in combination define 'PS-3523' as a unique variety distinguishing it from other closely related commercial varieties in the region:

1. Medium to large size plant, strong vigor;
2. high number of crowns per plant;
3. strong leaf gloss, deep serrations, medium to large stipules, few runners;
4. longer than broad fruit, small seed, conical fruit shape, marked to moderate differences in shape between primary and secondary fruit, orange red fruit color, very good fruit gloss and skin firmness;
5. slightly reflexed calyx;
6. long pedicels and peduncles; and
7. long fruiting trusses and fruit and flowers characteristically above the foliage.

The varieties which are believed to be most closely related to 'PS-3523' are 'PS-592', 'PS-1150' (U.S. Plant Pat. No. 10,780) and 'PS-1269' (U.S. Plant Pat. No. 10,686).

In comparison to the similar variety, 'PS-592', 'PS-3523' differs by the following combination of characteristics. The plant of 'PS-3523' is slightly smaller in size as compared to 'PS-592'. The foliage is slightly flatter in cross section, smaller in size with larger stipules and slightly more interveinal leaf blistering. The length to width ratio of the terminal leaflet is longer than broad as compared to much longer than broad for 'PS-592'. The fruit of 'PS-3523' is smaller in size, firmer with a smaller calyx and a darker internal color than 'PS-592'.

The difference in shape between primary and secondary fruit is greater between 'PS-3525' than 'PS-592'. The fruiting trusses have more anthocyanin than 'PS-592'. The fruit and flowers of 'PS-3523' tend to be more visible above the plant as compared to 'PS-592'.

In comparison to the similar variety, 'PS-1150', 'PS-3523' differs by the following combination of characteristics. The plant of 'PS-3523' is larger in size as compared to 'PS-1150'. The foliage is larger in size, stronger in interveinal leaf blistering, stronger in gloss with deeper serrations. Bract leaflets are larger in size and tend to occur much more often on the petioles. The fruit of 'PS-3523' is larger in size, lighter in color with better overall flavor than 'PS-1150'. The calyx segments tend to be slightly more reflexed with a greater difference in shape between primaries and secondaries as compared to 'PS-1150'. The fruiting trusses of 'PS-3523' tend to be longer in overall length with less anthocyanin as compared to 'PS-1150'.

In comparison to the similar variety, 'PS-1269', 'PS-3523' differs by the following combination of characteristics. The plant of 'PS-3523' is slightly larger in size as compared to 'PS-1269'. The foliage is slightly smaller in size, weaker in interveinal leaf blistering, stronger in gloss with deeper serrations. The length to width ratio of the terminal leaflet is longer than broad as compared to as long as broad for 'PS-1269'. The foliage of 'PS-3523' is much flatter in cross section as compared to 'PS-1269' which tends to be strongly concave. The fruit of 'PS-3523' is smaller in size and stronger in overall gloss with better appearance ratings. The internal flesh color is darker. The calyx segments tend to be slightly more reflexed. The fruiting trusses of 'PS-3523' tend to be longer in overall length with more anthocyanin as compared to 'PS-1269'.

For identification a series of molecular markers have been determined for this new variety.

BRIEF DESCRIPTIONS OF THE DRAWINGS

The accompanying color photographs show typical specimens of the new variety at various stages of development as nearly true as it is possible to make in color reproductions. The depicted plant and plant parts were approximately 7 to 9 months old.

DETAILED BOTANICAL DESCRIPTION

Figure 1:
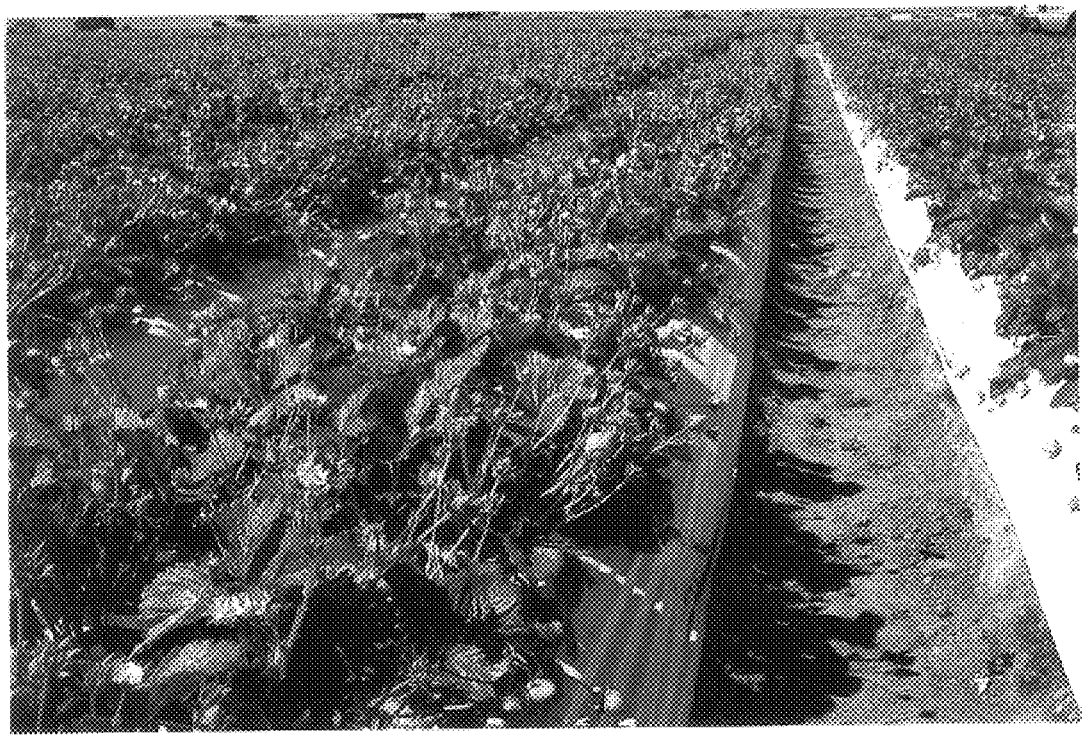
FIG. 1 shows typical fruiting field characteristics on Jun. 10, 2002.
Figure 2:
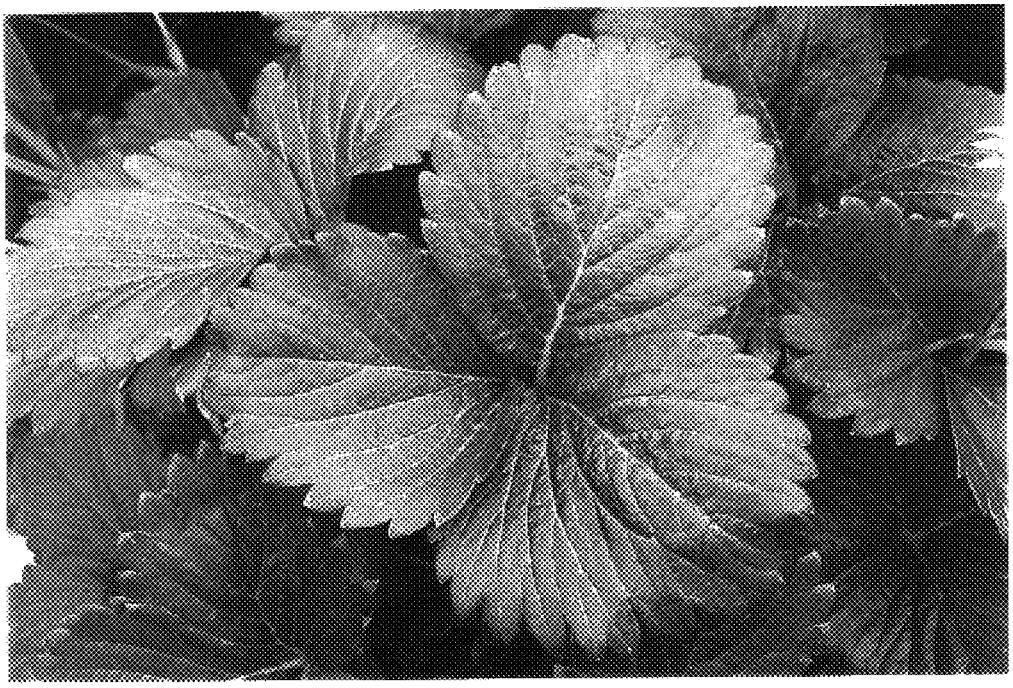
FIG. 2 shows a close-up view of a typical mature trifoliate on Jul. 3, 2002.
Figure 3:
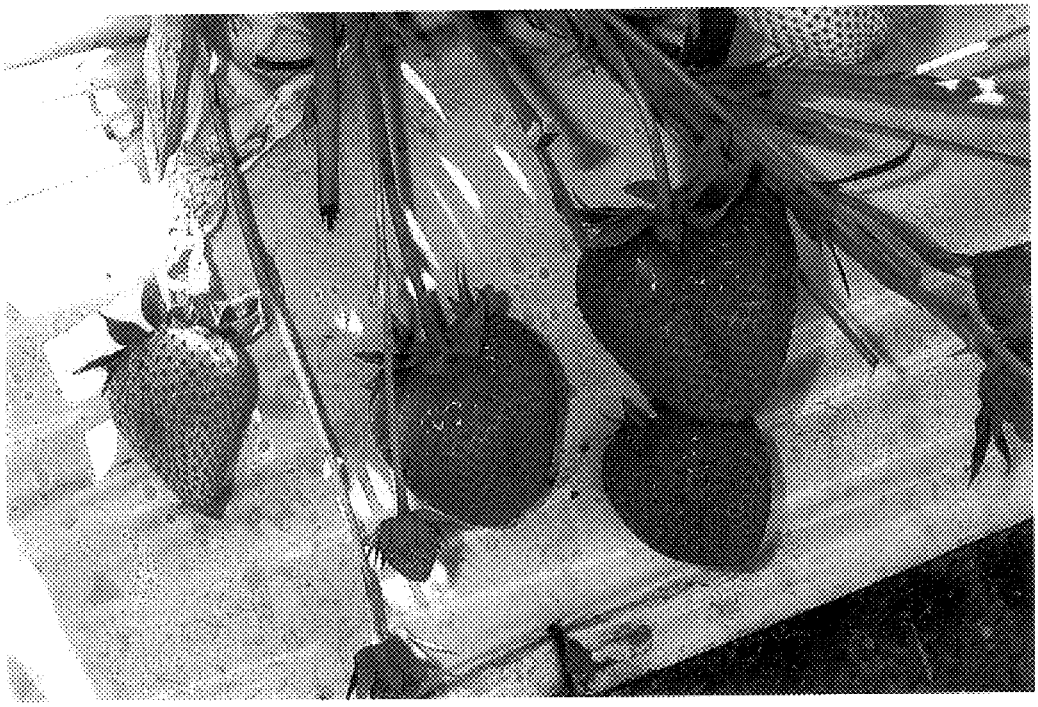
FIG. 3 shows typical mature and immature field fruit on Jun. 10, 2002.
Figure 4:
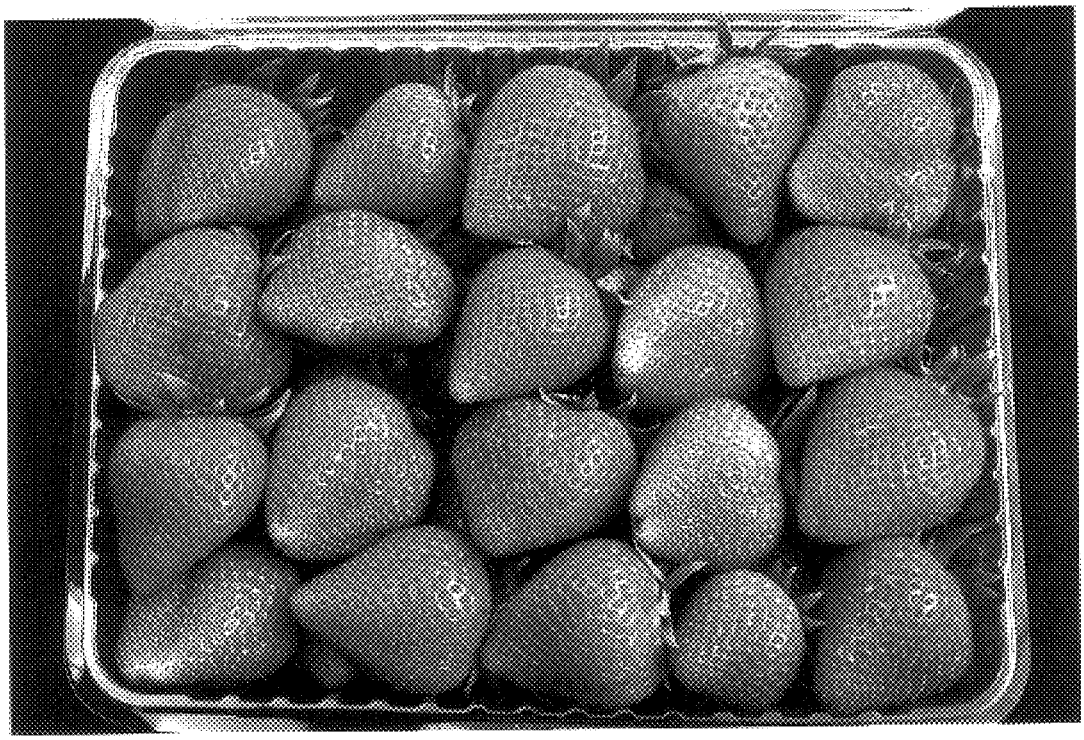
FIG. 4 shows a close-up view of fruit on Jul. 1, 2002.
Figure 5:
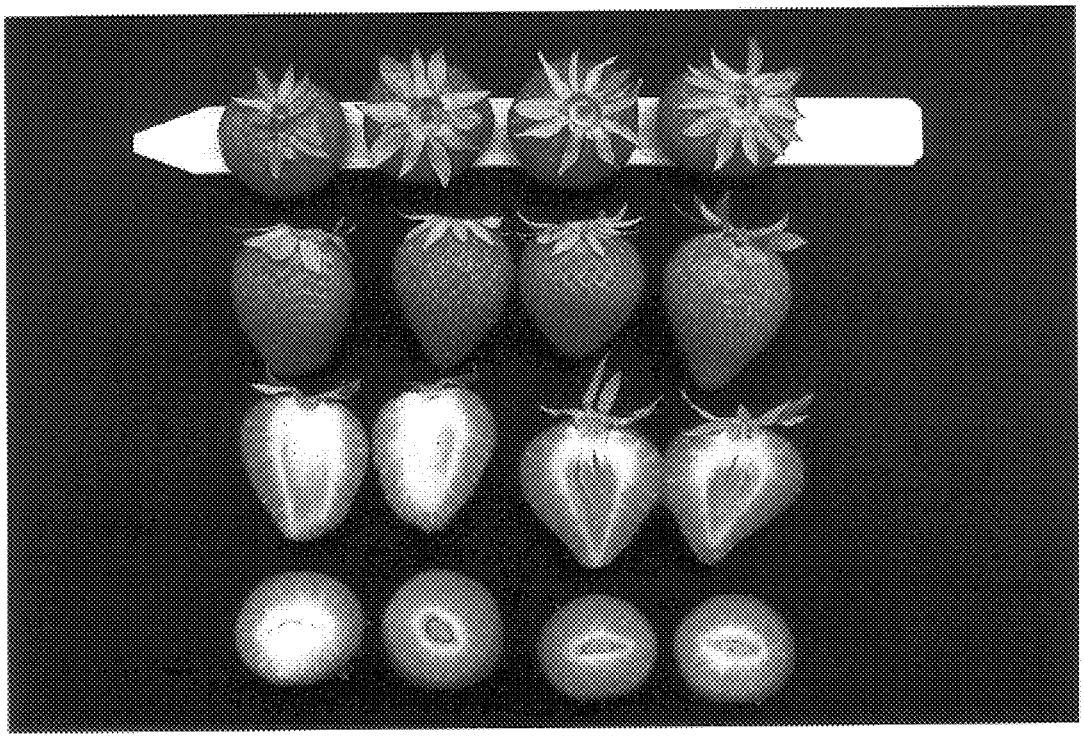
FIG. 5 shows typical internal and external fruit characteristics on Aug. 1, 2002.

The following description of 'PS-3523' unless otherwise noted, is based on observations taken during the 2002 growing season in Salinas, Calif. These measurements and ratings were taken from plants dug from a high-elevation nursery located in Siskiyou County, Calif. during the middle of October 2001 and planted approximately 3 weeks later in Salinas, Calif. The approximate age of the observed plants is 7 to 8 months. Yield observations and fruit quality characteristics are averaged from data collected during the 1999 through 2002 production seasons. The characteristics of the new variety may vary in detail, depending upon variations in environmental factors, including weather (temperature, humidity and light intensity), day length, soil type and location. 'PS-3523' has not been observed under all possible environmental conditions. Color terminology where noted follows the Munsell Book of Colors, Munsell Color, Baltimore, Md. (1976).

Fruit Characteristics

'PS-3523' fruit, fruit production and fruit quality characteristics. Fruit characteristics are taken from secondary fruit on a first year planting.

TABLE 1

1999–2002 market fruit yield, fruit size and runner production characteristics of 'PS-3523' from Salinas, California.

| Cultivar | 1999–2002 Average April/May Yield GM/PL | 1999–2002 Average Total Yield GM/PL | 1999–2002 Average Fruit Size GRM | 1999–2002 Average Runners/PL |
|---|---|---|---|---|
| 'PS-3523' | 233 | 1,585 | 23.6 | 0.2 |
| 'PS-592' | 255 | 1,633 | 24.3 | 0.4 |
| 'PS-1150' | 138 | 1,327 | 18.8 | 0.5 |
| 'PS-1269' | 263 | 1,454 | 24.7 | 0.4 |

Fruit was harvested from April through October 1999–2002. The plants of 'PS-3523' were dug from a high elevation nursery (Macdoel, California) during the middle of October and planted approximately 3 weeks later in Salinas, California. 'PS-3523' is compared to the following standards dug and planted comparably to 'PS-3523'.

TABLE 2

Comparison of secondary fruit characteristics of 'PS-3523', with standards from Salinas, California, Jun. 13, 2002.

| Character | 'PS-3523' | 'PS-592' | 'PS-1150' | 'PS-1269' |
|---|---|---|---|---|
| Munsell Color Range | 7.5R 3/10 to 4/10 | 7.5R 3/12 to 4/12 | 7.5R 4/10 to 3/8 | 7.5R 3/10 to 4/10 |
| Mature Fruit | | | | |
| Fruit Length mean (cm) | 3.96 | 3.95 | 3.79 | 4.13 |
| Fruit Width mean (cm)* | 3.39 | 4.02 | 3.86 | 3.95 |
| Fruit Length/ Width Ratio | 1.2 | 0.98 | 1.05 | 1.29 |
| Calyx Diameter mean (cm) | 4.9 | 5.4 | 5.1 | 5.2 |
| No. Sepals/ Berry | 13.6 | 14.1 | 14.7 | 14.2 |
| Seed Weight mean (mgs) | 0.53 | 0.6 | 0.5 | 0.6 |

*Width is measured across the widest part of the berry, typically across the shoulders

TABLE 3

Comparison of 1999–2002 fruit quality characteristics, including flavor and soluble solids of 'PS-3523', with standards from Salinas, California.

| Character | 'PS-3523' | 'PS-592' | 'PS-1150' | 'PS-1269' |
|---|---|---|---|---|
| Skin Firmness* | 8.3 | 7.7 | 8.3 | 8.1 |
| Fruit Appearance* | 7.9 | 7.9 | 8.2 | 7.3 |
| Fruit Gloss* | 8.2 | 8.2 | 8.5 | 7.2 |
| Flavor** | 3.2 | 3.4 | 3.0 | 3.2 |
| Soluble Solids*** | 8.6 | 10.0 | 8.1 | 9.6 |

TABLE 3-continued

Comparison of 1999–2002 fruit quality characteristics, including flavor and soluble solids of 'PS-3523', with standards from Salinas, California.

| Character | 'PS-3523' | 'PS-592' | 'PS-1150' | 'PS-1269' |
|---|---|---|---|---|

*Results are averaged from 4 years of replicated holding test performed from April through October 1999–2002. Ratings are based on a scale from 1–10; the higher the rating, the stronger the skin and more attractive and glossy the berry.
**Results are averaged from tests performed from May through September 2002. Ratings are based on a scale from 1–5; the higher the rating the better the flavor.
***Results are averaged from tests performed from May through September 2002. Soluble solid content is measured in percent Brix, with percent Brix being an indirect measurement of the sugar content in the fruit.

Fruit:

*Ratio of length/width.*—Slightly longer than broad.
*Size.*—Medium.
*Predominant shape.*—Conical.
*Difference in shapes between primary and secondary fruit.*—Moderate to marked.
*Band without achenes.*—Narrow.
*Unevenness of surface.*—Weak to medium.
*Color of mature fruit.*—Orange to red.
*Color of immature fruit.*—Light to medium whitish yellow (10Y 8.5/4 to 8/6).
*Evenness of color.*—Slightly uneven to even.
*Glossines.*—Strong.
*Insertion of achenes.*—Level with surface.
*Insertion of calyx.*—Level with to in the basin.
*Attitude of the calyx segments.*—Spreading to slightly reflexed.
*Size of calyx in relation to fruit diameter.*—Slightly to much larger.
*Adherence of calyx* (*when fully ripe*).—Strong.
*Firmness of skin.*—Strong.
*Firmness of flesh.*—Firm.
*Color of flesh.*—Medium red (7.5R 4/10 to 4/12).
*Distribution of red color of the flesh.*—Marginal and central.
*Hollow center.*—Weakly to strongly expressed.
*Receptacle color.*—Whitish (N9.25/84.2%R to N9/78.7%R).
*Seed color.*—Medium yellow to medium red (5Y 6/8 to 7.5R 3/8).
*Time of flowering* (*50% of plants at first flower*).—Medium to early.
*Time of ripening* (*50% of plants with first ripe fruit*).—Medium to early.
*Time of ripening* (*length of time from flower to maturity*).—27.2 days in mid summer.
*Type of bearing.*—Fully remontant.

Plant Characteristics

'PS-3523' plant characteristics. Plant characteristics are taken from a fully mature mid season plant.

TABLE 4

Comparison of plant characteristics of 'PS-3523', with standards from Salinas, California, Jul. 13, 2002.

| Character | 'PS-3523' | 'PS-592' | 'PS-1150' | 'PS-1269' |
|---|---|---|---|---|
| Plant Height mean (cm) | 29.7 | 34.1 | 26.4 | 27.6 |

TABLE 4-continued

Comparison of plant characteristics of 'PS-3523', with standards from Salinas, California, Jul. 13, 2002.

| Character | 'PS-3523' | 'PS-592' | 'PS-1150' | 'PS-1269' |
|---|---|---|---|---|
| Plant Spread mean (cm) | 33.1 | 35.4 | 28.2 | 30.7 |
| Crowns/Plant (mean) | 6.8 | 6.3 | 5.2 | 3.8 |

Plant:

*Size.*—Medium to large.
*Habit.*—Globose.
*Density.*—Medium.
*Vigor.*—Medium to strong.

Stolons:

*Number.*—Few.
*Anthocyanin coloration.*—Medium.
*Thickness.*—Thick.
*Pubescence.*—Medium.

Foliage Characteristics

'PS-3523' foliage characteristics. Foliage characteristics are taken from a fully mature tri-foliate during mid season.

TABLE 5

Comparison of leaf characteristics of 'PS-3523', with standards from Salinas, California, Jun. 13, 2002.

| Character | 'PS-3523' | 'PS-592' | 'PS-1150' | 'PS-1269' |
|---|---|---|---|---|
| Munsell Color Range (upper surface) | 5GY 3/4 to 4/4 | 7.5GY 4/4 to 3/4 | 7.5GY 4/4 to 3/4 | 7.5GY 3/4 to 3/6 |
| Terminal Leaflet Length mean (cm) | 8.2 | 10.0 | 7.9 | 8.4 |
| Terminal Leaflet Width mean (cm) | 7.6 | 8.6 | 6.9 | 8.5 |
| Terminal Leaflet ratio (L/W) | 1.08 | 1.20 | 1.10 | 1.00 |
| Petiole Length mean (cm) | 17.7 | 20.8 | 18.9 | 18.6 |
| Petiole Width mean (mm) | 4.5 | 5.4 | 4.1 | 4.7 |
| Petiolule Length mean (mm) | 9.8 | 12.1 | 9.2 | 12.9 |
| Serrations/Leaf | 16.5 | 20.1 | 21.0 | 22.6 |
| Serration Depth mean (mm) | 7.7 | 7.7 | 5.0 | 5.5 |
| Stipule Length mean (cm) | 3.3 | 3.0 | 3.2 | 2.9 |
| Stipule Width mean (cm) | 1.8 | 1.7 | 1.8 | 2.0 |

Foliage:

*Color of upper surface.*—Medium to light green.
*Color of under side.*—Medium gray green (7.5GY 5/4 to 6/4).
*Shape in cross section.*—Slightly concave to flat to slightly convex.
*Blistering.*—Medium to strong.
*Glossiness.*—Medium to strong.
*Number of leaflets/leaf.*—Three.

Terminal leaflet:

*Size.*—Medium.

*Length/width ratio.*—Longer than broad.
*Shape of base.*—Obtuse.
*Shape of incision of margins.*—Obtuse.
*Depth of serrations.*—Deep.

Petiole:
*Pubescence.*—Sparse.
*Stipule color.*—Light to medium green.
*Anthocyanin coloration of stipule.*—Medium to strong.
*Attitude of hairs.*—Slightly outward to strongly outward.
*Size of bract leaflets.*—Medium.
*Frequency of bract leaflets.*—Occur on approximatley 60% of the petioles.

Flowers and Inflorescences

'PS-3523' inflorescence and flower characteristics. Inflorescence characteristic are taken from a fully mature plant during mid season. Flower characteristics are taken from a secondary flower during mid season at full maturity:

TABLE 6

Comparison of inflorescence and secondary flower characteristics of 'PS-3523', with standards from Salinas, California, Jun. 12, 2002.

| Character | 'PS-3523' | 'PS-592' | 'PS-1150' | 'PS-1269' |
|---|---|---|---|---|
| Fruiting Truss Length* mean (cm) | 38.0 | 35.6 | 32.7 | 33.7 |
| Corolla Diameter mean (mm) | 28 | 31 | 30 | 30 |
| Calyx Diameter mean (mm) | 39 | 38 | 39 | 39 |
| Petal Length mean (mm) | 1.2 | 1.3 | 1.3 | 1.1 |
| Petal Width mean (mm) | 1.1 | 1.4 | 1.2 | 1.2 |
| Petal L/W Ratio | 1.09 | 0.93 | 1.08 | 0.92 |
| Petals/Flower (mean) | 6.6 | 6.7 | 7.1 | 7.1 |
| Sepal Length mean (mm) | 16 | 16 | 16 | 14 |
| Sepal Width mean (mm) | 6 | 5 | 6 | 7 |

TABLE 6-continued

Comparison of inflorescence and secondary flower characteristics of 'PS-3523', with standards from Salinas, California, Jun. 12, 2002.

| Character | 'PS-3523' | 'PS-592' | 'PS-1150' | 'PS-1269' |
|---|---|---|---|---|
| Sepal L/W Ratio | 2.7 | 3.2 | 2.7 | 2.0 |
| Sepals/Flower (mean) | 12.4 | 13.1 | 12.8 | 13.9 |
| Stamens/Flower (mean) | 29.3 | 31.2 | 30.8 | 27.3 |
| Pistils/Flower(mean) | 606 | 561 | 415 | 689 |

*as measured from the base of the primary peduncle where it attaches to the crown of the plant to the furthest berry.

Inflorescence:
*Position relative to foliage.*—Above.
*Pubescence.*—Weak.
*Anthocyanin.*—Moderate.
*Number of bract leaflets per truss.*—0 to 2.
*Size of bract leaflets.*—Medium to large.
*Fruiting truss length.*—Medium to long.

Flowers:
*Color.*—White.
*Size.*—Medium.
*Size of calyx relative to corolla.*—Larger.
*Relative position of petals.*—Touching to overlapping.
*Petal length/width ratio.*—Longer than broad.

Pest reactions: This new variety may not be resistant to any of the known insects, diseases or viruses common in California. It is known to be moderately susceptible to the two-spotted spider mite and aphid and may be slightly more susceptible to flower thrips. It is also known to be moderately susceptible to grey fruit mold and slightly susceptible to powdery mildew. The susceptibility of the new variety to any of the virus complexes of California has not been determined.

We claim:

1. A new and distinct strawberry plant named 'PS-3523', as herein described and illustrated by the characteristics set forth above.

* * * * *